US008148075B2

(12) United States Patent
Farrell

(10) Patent No.: US 8,148,075 B2
(45) Date of Patent: *Apr. 3, 2012

(54) METHODS FOR PRODUCING NUCLEIC ACID HYBRIDIZATION PROBES THAT AMPLIFY HYBRIDIZATION SIGNAL BY PROMOTING NETWORK FORMATION

(75) Inventor: Michael Patrick Farrell, Sugar Grove, IL (US)

(73) Assignee: Ventana Medical Systems, Inc., Tuscon, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/791,335

(22) Filed: Jun. 1, 2010

(65) Prior Publication Data

US 2010/0279304 A1    Nov. 4, 2010

Related U.S. Application Data

(63) Continuation of application No. 09/874,849, filed on Jun. 5, 2001, now Pat. No. 7,763,421.

(60) Provisional application No. 60/209,349, filed on Jun. 5, 2000.

(51) Int. Cl.
*C12Q 1/68* (2006.01)
*C07H 21/04* (2006.01)

(52) U.S. Cl. ........................... 435/6.11; 536/24.3

(58) Field of Classification Search .................. None
See application file for complete search history.

(56) References Cited

U.S. PATENT DOCUMENTS

| 5,124,246 A | 6/1992 | Urdea et al. |
| 5,849,481 A * | 12/1998 | Urdea et al. ................. 435/6.11 |
| 7,763,421 B2 * | 7/2010 | Farrell ............................. 435/6 |

FOREIGN PATENT DOCUMENTS

EP    0317077 B1    1/1996

OTHER PUBLICATIONS

Levy and Mattei, Chapter 9 "Applications of Chromosomal in situ Hybridization," in *Gene probes 2: A Practical Approach*, Hames and Higgins (eds.), pp. 211-243, Oxford University Press, 1995.

* cited by examiner

*Primary Examiner* — Samuel Woolwine
*Assistant Examiner* — Suchira Pande
(74) *Attorney, Agent, or Firm* — Klarquist Sparkman, LLP

(57) ABSTRACT

This invention describes methods for the generation of nucleic acid probes that improve the sensitivity of hybridization assays. The sensitivity increase results from structural modifications of nucleic acids that promote network formation during hybridization with the result that a single target molecule becomes attached to a complex of many probe molecules. The structural modification involves fragmentation of the probe nucleic acid followed by joining the fragments together such that their order and orientation and number is altered from the original probe molecule. The result is the generation of permuted probe libraries. Probes made according to this invention can be used in many kinds of hybridization assays including Southern blots. Northern blots. Dot blots. Nucleic acid Array hybridization, 'in situ' hybridization with fluorescent or other labels (FISH) and various kinds of sandwich hybridization assays.

12 Claims, 3 Drawing Sheets

FIG. 2

Some of many possible litigation products in a permuted probe library.

METHODS FOR PRODUCING NUCLEIC ACID HYBRIDIZATION PROBES THAT AMPLIFY HYBRIDIZATION SIGNAL BY PROMOTING NETWORK FORMATION

CROSS-REFERENCE TO RELATED APPLICATIONS

This is a continuation of U.S. application Ser. No. 09/874,849 filed Jun. 5, 2001, now U.S. Pat. No. 7,763,421, which claims priority to U.S. Provisional Patent Application 60/209,349 filed on Jun. 5, 2000.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

The ability of nucleic acids to bind their complementary sequences is the basis of assays for the detection of specific nucleic acid sequences. An available nucleic acid, the probe, can be modified to facilitate it's detection or it's separation from other nucleic acids. Various kinds of labels have been used. Radioactive or fluorescent labels can be introduced enzymatically or chemically. Enzymes can be chemically coupled to nucleic acid to generate the probe. Particular nucleic acid sequences can be coupled to a probe to facilitate it's detection by methods based on that sequence—e.g. polymerase reaction, ligase chain reaction, Q-beta replicase amplification, etc.

Generally, the target of such assays is a particular nucleic acid that represents a small fraction of the total sample. Consequently assay sensitivity is an important consideration and the various labels and methods have been designed with a view to attaining high sensitivity.

Conceptually in a simple hybridization assay two strands of complementary nucleic acid come together to form a double stranded structure. The probe strand contains a label and the target strand is detected by means of the labeled strand to which it becomes attached by hybridization.

The assay sensitivity depends on the amount of label captured in the hybridization complex. The label may be something that can be detected directly—e.g a fluorescent moiety or a colored substance (chromogen). The label may be something that can be detected indirectly. This would include a radioactive isotope, or particular nucleic acid template or sequence which functions as a ligand or as a target for subsequent hybridization to a different labeled nucleic acid. The label attached to the nucleic acid can be a chemical moiety to which something else binds which can itself be detected directly or indirectly. For example if the probe is modified by attachment of an antigen then specific antibody molecules can bind the antigen. Such antibodies may be detected directly if appropriately labeled e.g. with fluorescent moieties or indirectly after reaction with a second appropriately labeled antiserum. Either the first or second antiserum may be labeled with an enzyme e.g. alkaline phosphatase or peroxidase, the catalytic activity of which further enhances assay sensitivity. In addition to antigens, other moieties that bind to proteins may be used to label the probe. Biotin labeled probes can be detected after reaction with appropriately labeled avidin or streptavidin. Proteins that bind specific nucleic acid sequences can be used either alone or appropriately labeled or as part of fusion proteins with a partner which is itself detectable either directly or indirectly. Nucleic acids can be labeled by enzymatically or chemically attaching fluorescent or coloured molecules which can be directly detected. Particles, enzymes and polymeric substances or crystals with appropriate surface modifications can be used as direct or indirect labels for nucleic acids.

Both chemical and enzymatic methods are routinely used to place a label in the probe sequence. Short oligo-nucleotides are often labeled at the 5' end by using T4 polynucleotide kinase to introduce a radioactive phosphate. The 3' end is often labeled with T4 RNA ligase or with terminal transferase. Chemical modifications permit a great variety of labels to be introduced internally or at the ends of synthetic or naturally occurring nucleic acids. Large DNA molecules can be labeled internally by first reacting with bisulfite to generate amino residues to which NHS esters of labels (e.g., fluorescent dyes) can be readily coupled. A common way to introduce labels makes use of the nick translation activity of E. coli Pol I holoenzyme. The Klenow fragment of Pol T primed by short random oligo-nucleotides (e.g., hexamers or nanomers) provides a convenient and robust labeling method.

Whether the ultimate signal detection is direct or indirect, the amount of signal is dependent on the amount of label attached per unit mass of the probe molecules (for radioactive probes this is referred to as specific activity of the probe). There are practical limitations to how much signal-generating moiety can be incorporated into probe molecules without inhibiting assay performance. Labels that result in chemically modified nucleic acid, whether incorporated chemically or enzymatically, typically interfere with hybridization characteristics of a probe if more than a few percent of the nucleotide residues are modified. Presumably bulky side groups destabilize duplexes. A high concentration of label moieties can change the physical and chemical properties of the molecule, increasing susceptibility to cleavage as occurs with radioactive probes or increasing stickiness for example as occurs with fluorescent labeled probes. This can result in poor hybridization or in high non-specific binding both of which limit assay sensitivity.

This invention is a method for modifying the DNA sequence prior to or during labeling so as to promote network formation during hybridization with the result that each target sequence becomes attached to many labeled probe molecules. The assay sensitivity is thereby increased. This can be applied to many kinds of hybridization assay. Particular applications include hybridization to nucleic acid arrays, in situ hybridization, dot blots, Southern blots, Northern blots, sandwich hybridization assays etc.

BRIEF SUMMARY OF THE INVENTION

Consider a piece of double stranded deoxyribonucleic acid labeled by nick translation and illustrated in FIGS. 1a and 1b. The label, represented by an asterisk, is distributed intermittently throughout both strands. If such a piece of DNA is denatured (e.g. by heating) to separate the strands and then annealed to denatured target DNA, hybrids form in which the labeled probe strand is annealed to a complementary target strand as shown in FIG. 1c. This is a standard hybridization reaction.

Now consider the same piece of DNA shown in FIG. 1a, but fragmented (e.g., by a restriction endonuclease). If the mixture of fragments is ligated together (e.g., by T4 DNA ligase) they will come together in a variety of permutations and orientations and numbers to form a complex mixture of double stranded fragments partially illustrated in FIG. 2. This is called a permuted probe library. An individual member of the library has a particular size resulting from a fixed number of copies of each segment in fixed order and orientation relative to each other. Individual members can be isolated as discussed below. In many applications the entire library can be used as a probe. In some applications it is advantageous to isolate one or a number of library members and to propagate them individually and to use them either alone or mixed together or mixed with non-permuted probe DNA as probes.

Now consider what happens if this permuted probe library is denatured and annealed to target DNA homologous to the original non-fragmented probe molecule. FIG. 3 illustrates a hybrid formed by annealing of the top strand of the original target sequence to one member of the population of molecules generated by the fragmentation and ligation procedure. Note that products formed by annealing one segment of the ligation product to a target molecule preclude the annealing of other segments of the same probe molecule to the same target molecule. Some segments of the ligated product cannot anneal to the target molecule because the corresponding region is identical rather than complementary to target because of the orientation of that segment in the ligated product. Other segments of the ligated product cannot anneal to the corresponding segment of target because the order of segments has been altered or because a segment is absent from the probe molecule. Nevertheless, although some probe segments are not hybridized to their complementary sequence in the target they remain attached to the target because of the hybridization of adjoining segments.

The result of annealing this one ligation product to a target molecule is a complex that retains multiple single stranded segments both in the target and in the probe. Additional probe molecules can anneal to these single stranded segments. Further annealing of probe molecules to the complex results in a larger complex which also retains single stranded segments to which further probe molecules can anneal. Each target molecule eventually acquires many labeled probe molecules. This is minimally illustrated in FIG. 4 which shows single target molecules annealed to one, two and four molecules of permuted probe.

This contrasts with the standard hybridization reaction described above and illustrated in FIG. 1 where only one target equivalent of probe is able to provide hybridization signal. The permuted probe provides a higher signal than the standard probe.

1A: The straight lines represent the strands of a piece of double stranded DNA. Upper case letters indicate points at which the DNA is to be cleaved, e.g. by a restriction endonuclease, to generate fragments which can be ligated together in various orders.

Figure 1:
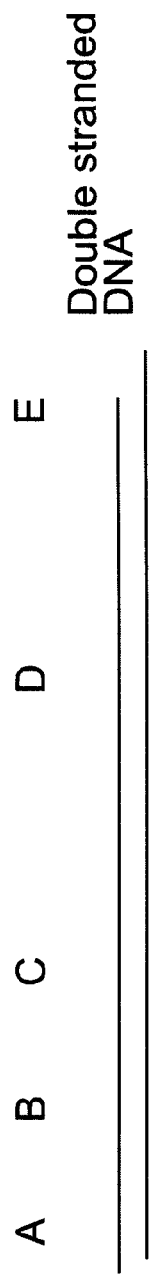
FIG. 1
Figure 3:
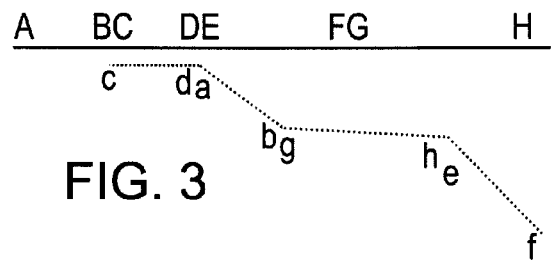
Figure 4:
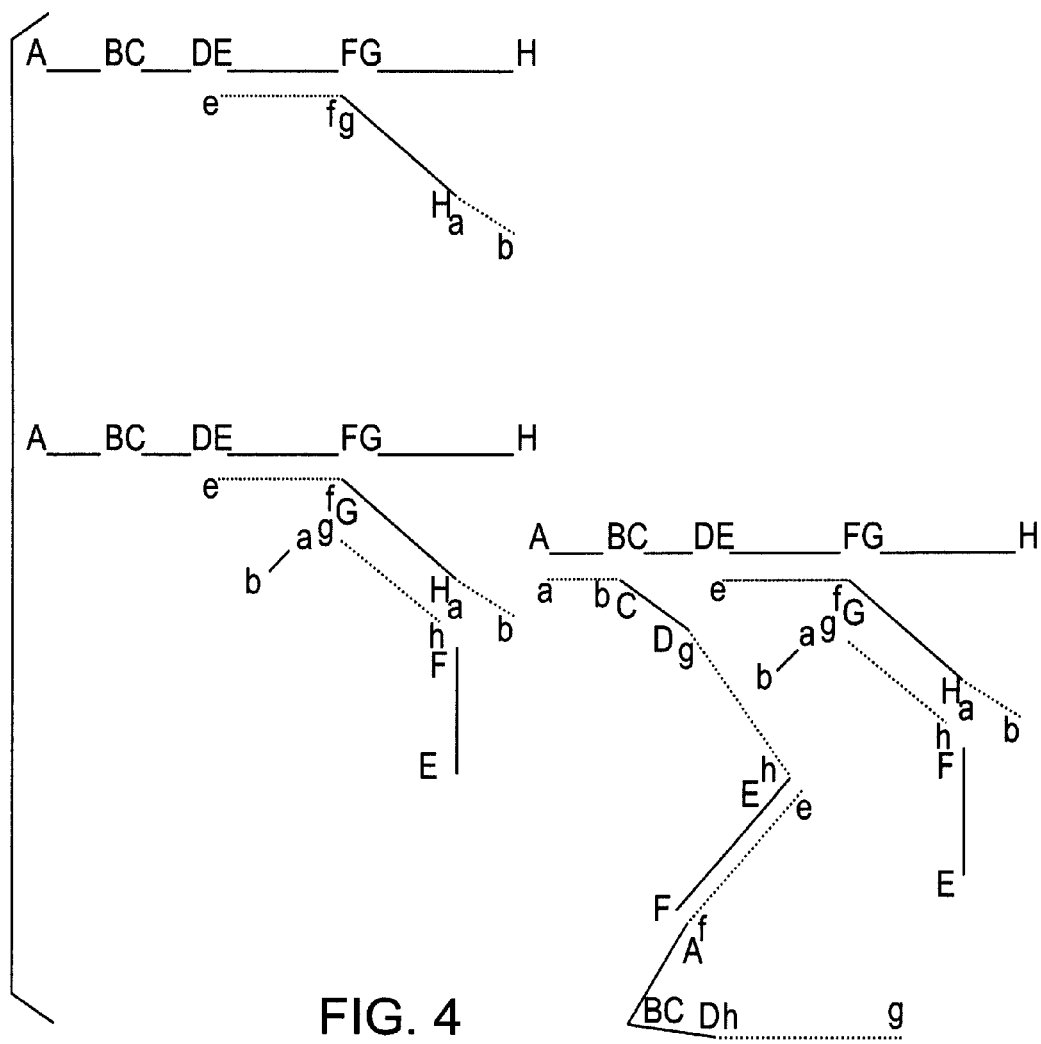

1B: This represents the same piece of DNA shown in FIG. 1A but after being labeled by nick translation to incorporate labeled nucleotides (e.g., radioactive or fluorescent or chemically reactive nucleotide derivatives). The asterisks represent the labels. The illustration is not meant to imply that the strands have been broken. Note that the label is distributed throughout both strands of DNA.

1C: This shows the hybridization product resulting from denaturation of the labeled DNA shown in FIG. 1B and it's hybridization to denatured DNA from FIG. 1A. The top strand shows the labeled probe which is annealed to the bottom strand of the non-labeled target sequence from FIG. 1A.

FIG. 2

Part 1: This shows the double stranded DNA from FIG. 1a but after being cleaved by a restriction endonuclease. The upper case letters and bold line represent the top strand of the original DNA molecule. The lower case letters and dotted line represent the bottom strand of the original DNA molecule. The fragments are shown in their original order. All fragments are considered to have flush ends in this case.

Parts II, III, IV, and V show some of the products formed by ligation of the mixture of fragments shown in FIG. 2 part I. Note that a given ligation product can include any fragment in either of the two possible orientations. A fragment may be absent from a given ligation product or it may be present once or more than once and in more than one orientation. A collection of such ligation products is referred to as a permuted probe library.

FIG. 3

This shows a strand of one ligation product, as described in FIG. 2, hybridized to the original non-permuted target DNA. The upper case letters and bold line represent the top strand of the original DNA molecule. The lower case letters and dotted line represents a permuted DNA molecule. In this case the permuted molecule contains fragments that have been ligated in their original orientations relative to each other but their order has been changed. Note that hybridization of certain segments to target interferes with hybridization of adjoining fragments to target. In reality, of course, the DNA is flexible. Nevertheless hybridization interference results in residual single stranded regions on both probe and target.

FIG. 4

This illustrates three simple hybridization products resulting from annealing the original non-permuted target to permuted probe molecules. Hybridization products containing a single target molecule with one, two and four molecules of permuted probe are shown. All hybridization complexes retain single stranded regions to which additional probe molecules can hybridize to increase the complex size and signal strength.

DETAILED DESCRIPTION OF THE INVENTION

This invention concerns methods for improving hybridization assays by modifying probe nucleic acid so as to promote network formation during hybridization. The probe can be modified in various ways and the labeling of probe can be done by various methods. Hybridization assays can be done in various ways to take advantage of the probe modifications.

Probe Modification Methods

1. Consider an available probe composed of double stranded DNA containing a sequence corresponding to a specific target nucleic acid. A simple way to fragment this DNA is by digestion with a restriction endonuclease. If the resulting mixture of digestion products is then ligated together using T4 DNA ligase the results is a variety of double stranded DNA products each composed of a permuted combination of fragments from the digest. A given product may contain any or all or some of the fragments from the digest. A given fragment may be absent or present once or present in more than one copy. A fragment may be present in either of the two possible orientations with the result that a sequence which was present in one strand of the original probe molecule may now be juxtaposed to and co-linear with a fragment from the other strand of the original probe. This is illustrated in FIG. 2. The ligation products are double stranded DNA and can therefore be labeled by standard nick translation procedures or by other procedures routinely used to label DNA.

2. The restriction endonucleases used for fragmentation may have a long or short recognition sequences and cut DNA with high or low frequency. The enzyme and may cut to leave DNA with flush ends (e.g., Alu I) or sticky ends which promote ligation (e.g., Sau3A I). If a class 2S restriction endonuclease is used and produces fragments with sticky ends then only certain combinations of fragment can be ligated together. This can be taken advantage of to design probes with control of network formation. Fragmentation can also be done using more than one enzyme. A double digest with Alu I and Hae III would reduce most probe sequences to small fragments with flush ends which can be ligated together to generate a diverse population of permuted products. A linear DNA molecule can have it's terminal 5' phosphates removed by treatment with a phosphatase (e.g., shrimp alkaline phosphatase). If such dephosphorylated DNA is subjected to the fragmentation and ligation procedure then whenever one of the dephosphorylated fragments is ligated it's dephosphorylated 5' end would block ligation of additional fragments to that strand of the product. After denaturation such ligation products would be terminated at the 5' end largely with the original terminal fragments. This permits further control of network formation. It is also useful if individual library members are to be isolated by peR because the sequence of the 5' terminal fragment may be known and can therefore be used for primer design. In some cases it could be desirable to remove one of the dephosphorylated ends prior to fragmentation so that most ligation products would end with the same terminal fragment. Alternatively, a specially designed non-phosphorylated oligonucleotide might be annealed to a 5' phosphorylated complementary oligonucleotide such that the resulting double stranded fragment could take part in the ligation reaction but would terminate ligation in the dephosphorylated strand whenever incorporated into the product. This would be useful if it is desired to produce an RNA probe corresponding to the library of permuted DNA probe sequences. The designed oligonucleotide would encode a promotor for an RNA polymerase (e.g. T7 RNA polymerase). The ligation products can then be transcribed with the polymerase to produce RNA probe which can be labeled during or after transcription.

3. Fragmentation can be done without using restriction endonucleases. This can provide a more diverse library of fragments for ligation. One way to do this is to use a nuclease such as DNAaseI and to digest for a time and at an enzyme concentration sufficient only to partially digest the probe DNA. The DNAase I can be inactivated or removed prior to ligating the products to generate the permuted probe library for labeling. Partially digested products of a desired size may be isolated after a fractionation procedure (e.g., gel electrophoresis) prior to ligation.

4. Another way to fragment DNA is to perform the DNAase 1 digestion in the presence of manganese rather than magnesium, which is the standard cofactor. Replacing magnesium by manganese results in most of the DNA being digested to a size close to 50 nucleotides but no smaller. After purification such fragments can be ligated together to produce the permuted probe for labeling. No size fractionation is needed if this method is used. (Pastan).

5. Ligation of fragmented DNA can be promoted by first treating the DNAase1 products with the Klenow fragment of Poll and dNTP's to render flush any staggered ends which may be in the population. A further ligation enhancement can be achieved by ligating the probe fragments to a double stranded linker oligonucleotide with one flush and one sticky end to supply sticky ends that facilitate ligation of the probe fragments.

6. Fragmentation can be done by physical methods—e.g. by repeated pressurized passes through small apertures or by sonication. Heating can also fragment DNA. Repeated autoclaving for short intervals allows DNA fragmentation to be controlled. For example total cellular DNA can be reduced to a few hundred nucleotides in size by autoclaving for several five minute intervals. The total time of exposure to high temperature can be used to control the size of the products obtained Annealing followed by Klenow treatment plus dNTP's regenerates the double stranded DNA with ends appropriate for the ligation step.

7. Fragmentation can be done by chemical methods. For example the various reactions used in the sequencing of DNA by chemical methods can be used. Because these often result in single stranded fragments the products may have to be annealed and treated with Klenow fragment of Poll and dNTP's as described above to promote ligation to generate the permuted probe sequences for labeling.

Probe Permutation Methods

When probe fragmentation has been done in one of the ways described above the invention requires that fragments be recombined so as to produce fragment combinations that promote network formation during hybridization. One way to do this is by ligating the fragments together using T4 DNA ligase or an equivalent enzyme. If the fragments do not have efficiently ligatable sticky ends such as those produced by many restriction endonucleases (e.g., Msp I or Sau3A I) then ligation can be enhanced by enzymatic treatments described above prior to ligation for permuted probe generation. Ligation can also be done by chemical rather than enzymatic methods e.g., Cyanogen Bromide ligation of DNA in DMSO. Fragments can also be joined or cross-linked by chemical linkages not typical of biological molecules. This can be facilitated by chemical modifications of the DNA. For example, bisulfite treatment of DNA in the presence of ethylene diamine generates reactive amino groups on cytosine residues such that the extent of this modification can easily be controlled by the incubation time. Such modified DNA fragments can be easily crosslinked by means of various bi-functional cross-linking agents. e.g., homo-bi-functional N-hydroxy succinimide esters such as Bis(sulfosuccinimidyl)suberate (PIERCE). Such cross-linked probes would form networks during hybridization as described in this invention.

Permutation Enhancement

Consider the mixture of products resulting from probe fragmentation and ligation by T4 DNA ligase as described above. This is a mixture of DNA ligation products of various sizes and with each of the component segments present in various numbers of copies, each copy being present in one of the two possible orientations. For simplicity suppose that one of these ligation products is isolated from the others and randomly cleaved to generate a collection of small fragments as with DNAaseI and that this collection subjected to repeated cycles of denaturation, annealing and polymerization. When such a mixture is subjected to a cycle of denaturation and renaturation under conditions in which DNA polymerase activity can take place complementary fragments with non-identical ends anneal and prime synthesis on each other resulting in elongation of one or both fragments. Further repeated cycles result in the generation of fragments of progressively greater size. The amount of probe produced would be greater than the amount originally subjected to the post purification fragmentation procedure since net DNA synthesis takes place at each cycle. Aliquots of the product can be taken and labeled by standard methods, e.g. nick translation. Other aliquots could be taken and re-fragmented and reamplified to generate subsequent generations of this permuted probe fragment. A single ligation product of this type can be obtained by using PCR with a particular set of primers and isolation of a size class by gel electrophoresis. Enrichment by further cycles of PCR amplification and dilution would produce a single such product which can be repeatedly amplified using the chosen set of primers. By choosing primers from the same strand (rather than complementary strands) of the original pre-permutation probe it can be ensured that permuted molecules are amplified. In some applications a set of such individual permuted amplicons might be chosen and used as a permanent source of probes. This would increase control over and reproducibility of network formation during hybridization. The use of primers in this way facilitates the addition of desired nucleic acid sequence to one or both ends of the permuted probes. For example an amplification can be done using modified primers to introduce promoter sequences (e.g., for T7 RNA polymerase) at one end so that single stranded RNA probes can be made by transcription from the permutated probe template. Such probes can also form networks during hybridization. The double stranded RNA forming the network may be advantageous in some applications.

If instead of isolating one of the ligation products for use in the amplification procedure, the entire mixture of products is used then the result is an even more heterogeneous mixture of amplified permuted probe segments. The result is formation of an even more heterogeneous network during hybridization. This mixture can be further amplified by repeating the random fragmentation and amplification process. Or sets of individual permutation products can be isolated as described above and used indefinitely as sources of permuted probe.

Individual members of a permuted probe library can be isolated in various ways. For example: An oligonucleotide with sequence not related to the probe can be ligated to the permuted probe library. If PCR is carried out using a non-phosphorylated primer for this oligonucleotide and a phosphorylated primer corresponding to a sequence known to lie within the probe molecule, a variety of products will result. If these products are size fractionated by gel electrophoresis and molecules of a certain size purified the result is a collection of permuted probe molecules with a known terminal non-probe sequence and a known terminal probe sequence separated by an unknown combination of probe fragments. Various combinations of internal fragments can produce the same sized product. Ligation of a second oligonucleotide (the sequence of which is not otherwise represented in the probe) to this collection results in it being ligated only at the end which terminated in the phosphorylated probe sequence. Normal PCR can now be used to amplify aliquots of the mixture. By successive terminal dilutions followed by PCR using the two external primers, molecular clones of individual members of the library can be obtained. Members can be distinguished by restriction enzyme digestion and product fractionation. By this means a set of permuted probes can be obtained and indefinitely maintained and produced by PCR amplification. Such probes can be labeled during production by PCR by incorporation of modified nucleotides into the mixture or after production by one of the standard enzymatic or chemical methods—eg nick translation or chemical modification and conjugation to label moieties. These probes can be mixed in various proportions with each other and with non-permuted probe and labeled by various methods for use in hybridization assays where they promote network formation. The use of controlled mixtures of permuted probes increases assay reproducibility and provides control over the extent of network formation.

Modification of Permutation Mixture

The permutation method described above, fragmentation and ligation, produces collections of permuted probe molecules in which the proportions of the various sequence segments is the same as in the original probe molecule. In some applications it may be advantageous to add a sequence element to the mixture prior to the ligation step so that this extra element becomes incorporated into the permuted probe. The proportion of such an element can be chosen in advance. For example suppose that the probe is a papillomaviral genome composed of 7,000 base pairs. Fragmentation of one microgram of this double stranded DNA by DNAase1 with Manganese produces a collection of fragments about 50 bp in length. If one microgram of an unrelated double stranded DNA fragment 50 bp long (Call this an extra-target segment or sequence since it has no counterpart in the target sequence.) is added to the mixture prior to treating with the Klenow fragment of PolI with dNTP's to make the ends flush and the resulting mixture is ligated with T4 DNA ligase the result is a collection of permuted molecules in which, on average, every second DNA segment is the extra-target DNA in one of the two possible orientations. One consequence of this is increased density of the network. The high frequency of the non-viral segment results in a shorter distance between crosslink points and faster kinetics of network formation. The non-viral segment is also a potential target for annealing to a secondary detector probe—e.g. a fluorescence labeled oligonucleotide complementary to one or both strands of the extra-target segment. The high frequency of the extra-target segment in the permuted probe network further increases assay sensitivity and improves assay kinetics. Furthermore since the sequence of the extra-target segment can be designed, it can be chosen to have properties particularly appropriate for the application. And of course if multiple permuted probes are being used on a single sample to detect multiple targets simultaneously then different non-interacting extra-target sequences can be inserted into each permuted probe.

A major advantage of using permuted probes, which enhance network formation, is that targets too small to be detected by standard probes can be detected by this method. For example, in-situ hybridization with fluorescent labeled DNA probes (FISH) permits easy detection of single copy targets only when the probe is close to 100,000 base pairs long. Eukaryotic DNA of this size usually contains repeated DNA sequences that occur in more than one place in the genome. One result of this is a requirement in hybridization for blocking DNA made up of highly repeated sequences (COT I DNA) which are not labeled. This reduces background caused by probe hybridization outside the region of interest. If smaller DNA segments e.g. cDNA's rather than the corresponding genomic sequences can be used as probes then Cot 1 DNA is not required. This greatly facilitates probe identification and production. Furthermore, single copies of viral genomes, too small for detection by standard probes, may be detected by means of the probes described here.

What I claim as my invention is:

1. A method of detecting a target nucleic acid sequence, comprising:

hybridizing a nucleic acid probe composition to the target nucleic acid sequence, wherein the nucleic acid probe composition comprises a plurality of linear nucleotide sequence probes, at least some of which probes comprise a permuted combination of segments of a sequence complementary to the target nucleic acid sequence and segments of the target nucleic acid sequence, wherein the segments of the target nucleic acid sequence and the segments of a sequence complementary to the target nucleic acid sequence are not arranged in the same linear order as found in the target nucleic acid sequence;

generating a target sequence bound to a network of probe molecules; and detecting the target nucleic acid sequence.

2. The method of claim 1, wherein the plurality of linear nucleotide sequence probes further comprises nucleotide segments not represented in the target sequence, so that hybridization of such probes to the target sequence results in residual probe segments not annealed to the target sequence but which can anneal to other probe molecules with the result that a network of probe molecules is formed in which the target sequence is bound by more than one molar equivalent of probe.

3. The method of claim 1, wherein detecting the target nucleic acid sequence comprises detecting the network of probe molecules by a secondary agent.

4. The method of claim 3, wherein the secondary agent comprises a labeled nucleic acid that can anneal to single-stranded segments of the network of probe molecules.

5. The method of claim 3, wherein the secondary agent comprises a ligand that can anneal to single-stranded segments of the network of probe molecules.

6. The method of claim 1, wherein the target nucleic acid sequence is a target DNA sequence.

7. The method of claim 1, wherein the nucleic acid probe composition is generated by a method comprising:

fragmenting the target nucleic acid sequence, thereby producing a mixture of digestion products; and ligating the mixture of digestion products, thereby producing a nucleic acid probe composition comprising a plurality of double-stranded DNA linear nucleotide sequence probes.

8. The method of claim 7, wherein the fragmenting comprises digesting the target nucleic acid sequence with a restriction endonuclease or a nuclease.

9. The method of claim 7, further comprising labeling the nucleic acid probe composition.

10. The method of claim 9, wherein the labeling is performed using nick translation.

11. The method of claim 7, further comprising denaturing the nucleic acid probe composition comprising a plurality of double-stranded DNA linear nucleotide sequence probes, thereby producing a nucleic acid probe composition comprising a plurality of single-stranded DNA linear nucleotide sequence probes.

12. The method of claim 11, further comprising labeling the nucleic acid probe composition.

* * * * *